Patented Mar. 16, 1943

Plant Pat. 573

UNITED STATES PATENT OFFICE

573

PLUM

Frederic W. Anderson, Merced, Calif.

No Drawing. Application November 19, 1941,
Serial No. 419,697

1 Claim. (Cl. 47—62)

This invention relates to a mutation of the President Plum and is characterized by the later ripening of its fruit.

In 1934 one limb of a President plum tree in my thirty acre President block near Merced was noticed to produce fruit that was still green at the regular harvest period. It colored about two weeks later and remained firm until frost.

It was immediately propagated asexually by topworking other trees and its later ripening character has persisted, and seems identical to President otherwise.

Any standard description of the extensively grown President Plum would describe this new variety in all respects except the ripening date. However, the chief characteristics of this new variety are set forth below:

Tree: Large, vigorous; upright—spreading; productive.

Leaves: Nearly flat, obovate, one and three-quarters inches wide and three and one-quarter inches long, upper surface shining and lower surface without pubescence, margin crenate, petiole about three-quarters inch long.

Fruit: Late in ripening, about mid-September here.

*Size.*—Unusually large—two and one-quarter by two inches.

*Form.*—Elongated—oval with equal halves, suture shallow, cavity shallow and apex flattened.

*Color.*—Dark blue with heavy bloom.

*Skin.*—Thin but tough.

*Flesh.*—Light yellow, juicy, firm, sweet, mild.

*Pit.*—Free, one and one-eighth by seven-eighths inch in size.

*Quality.*—Good with excellent shipping and keeping characteristics.

Having thus described my discovery, I claim:

A new variety of plum tree as herein disclosed, characterized by producing fruit identical with the well known President Plum except that it ripens approximately two weeks later and thus prolongs the harvesting and marketing season of this standard variety.

FREDERIC W. ANDERSON.